United States Patent [19]

Cabré Castellví et al.

[11] Patent Number: 4,965,358

[75] Date of Patent: Oct. 23, 1990

[54] N,N'-CARBONYL-BIS-(4-ETHYL-2,3-DIOXO)-PIPERAZINE

[75] Inventors: Juan Cabré Castellví, Barcelona; José Diago Meseguer, Granollers; Asunción Esteve Bianchini, Barcelona; Carlos E. Lenhardt Padró, Alella; Esteve Sans Pitarch, Barcelona, all of Spain

[73] Assignee: Gema, S. A., Barcelona, Spain

[21] Appl. No.: 269,916

[22] Filed: Nov. 10, 1988

[30] Foreign Application Priority Data

Nov. 16, 1987 [ES] Spain .................................. 8703260

[51] Int. Cl.$^5$ ........................................... C07D 403/02
[52] U.S. Cl. .................................. 544/357; 540/217; 540/222; 540/227; 540/316; 544/229; 544/385
[58] Field of Search ........................................ 544/357

[56] References Cited

U.S. PATENT DOCUMENTS

| | | | |
|---|---|---|---|
| 3,763,091 | 10/1973 | Crescenzi et al. | 544/357 |
| 4,110,327 | 8/1978 | Saikawa et al. | 544/357 |
| 4,110,328 | 8/1978 | Diamond | 544/357 |
| 4,200,744 | 4/1989 | Saikawa et al. | 540/221 |
| 4,436,921 | 3/1984 | Hori et al. | 544/357 |

FOREIGN PATENT DOCUMENTS

| | | |
|---|---|---|
| 2600880 | 7/1977 | Fed. Rep. of Germany . |
| 2702552 | 7/1977 | Fed. Rep. of Germany . |
| 10688377 | 7/1977 | Japan . |

OTHER PUBLICATIONS

Derwent Abstract, Belgium 837682 (1976).
Derwent Abstract, Japan 52-19685 (1977).
Derwent Abstract, Europe 131174 (1985).
Derwent Abstract, Japan 52106883 (1977).
Derwent Abstract, Germany 26800880 (1977).
Derwent Abstract, Germany 2702552 (1977).
Chem. Abst., 104:148590d, Yao et al., Synthetic Studies of Piperacillin, 1985.

Primary Examiner—Donald G. Daus
Attorney, Agent, or Firm—Scully, Scott, Murphy and Presser

[57] ABSTRACT

A new compound called N,N'-carbonyl-bis-(4-ethyl-2,3-dioxo)-piperazine of Formula I

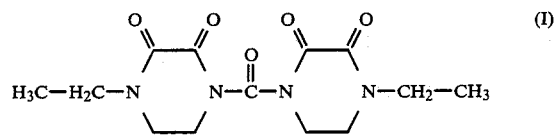

A process for the preparation thereof based on the reaction of 4-ethyl-2,3-dioxo-piperazine or a trimethylsilyl derivative thereof with carbonyl chloride or a derivative thereof.

The use of the compound of Formula I as an intermediate in the preparation of compounds of Formula II

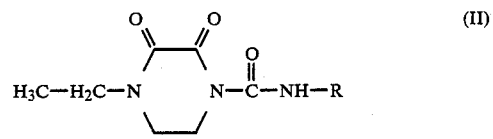

where R is a radical, substituted in alpha position, of a molecule of an acid selected from the group formed by phenylacetic acid, p-hydroxy phenylacetic acid, a 6-(phenylacetamido)-penicillanic acid and a 7-(phenylacetamido)-cephalosporanic acid.

1 Claim, No Drawings

N,N'-CARBONYL-BIS-(4-ETHYL-2,3-DIOXO)-PIPERAZINE

The invention relates to a new compound, N,N'-carbonyl-bis-(4-ethyl-2,3-dioxo)-piperazine of Formula I,

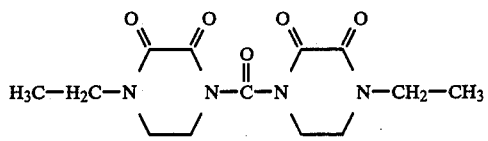

to a process for the preparation thereof and to the use thereof for the preparation of compounds of Formula II

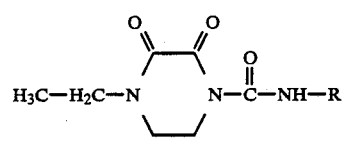

where R is a radical, substituted in alpha position, of a molecule of an acid selected from the group formed by phenylacetic acid, p-hydroxy phenylacetic acid, a 6-(phenylacetamido)-penicillanic acid and a 7-(phenylacetamido)-cephalosporanic acid.

The compounds of Formula II are of interest as beta-lactamic antibiotics or as intermediates for the preparation thereof. Piperacillin and cefoperazone may be cited as among such antibiotics.

The preparation of ((4-ethyl-2,3-dioxo)-piperazin-1-yl)-carboxylic acid derivatives, using preferably acid chloride, has been described in the technical literature.

Japanese patent application No. 106883/77 teaches the preparation of ((4-ethyl-2,3-dioxo)-piperazin-1-yl)-carbonyl chloride by reacting 4-ethyl-2,3-dioxo-piperazine with carbonyl chloride (phosgene). To this end, the N-trimethylsilyl derivative is preferably used. Japanese patent application No. 19685/77 describes, furthermore, the preparation of N-trichloro-methoxy-carbonyl using diphosgene or tri-chloromethyl chloroformate instead of phosgene. With this latter piperazine derivative, the yield is 44% piperacillin, according to the results of Qingxiang and Renyong (Chem, Abs. 104, 148590d).

The 1-chloro-carbonyl or the 1-trichloromethoxy-carbonyl derivative of piperazine is reacted with beta-lactamic antibiotics having an amino acid side chain, preferably phenylglycine and p-hydroxyphenylglycine derivatives, such as ampicillin and amoxycillin. An alternative method describes the prior reaction of the 1-chlorocarbonyl derivative of 4-ethyl-2,3-dioxo-piperazine with the amino acids and the resulting product is thereafter combined with a 6-aminopenicillanic or 7-aminocephalosporanic acid.

Thus EP No. 131.174 describes the use of the amino acid 2-chloro-4,5-dihydroxyphenylglycine and the 1-chlorocarbonyl derivative of 4-ethyl-2,3-dioxo-piperazine. The latter compound is used in Belgian patent No. 837682 and in German patent application No. 2.600.880 for the preparation of the N-piperazincarbonylamido derivatives of cephalosporins having a p-hydroxyphenylglycine side chain, with the preparation of cefoperazone being described.

German patent application No. 2.702.552 teaches that the acylation of a 7-aminocephalosporin gives a 61% yield when using the ethoxyformic anhydride of D(−)-alpha-(4-ethyl-2,3-dioxo-1-piperazinyl-carbonylamino)-phenylacetic acid and U.S. Pat. No. 4,200,744 teaches the use of acid chloride instead of the above anhydride. The acid is prepared according to AU No. 518.792 with an 87% yield by reacting D(−)alpha phenylglycine with 1-chlorocarbonyl-4-ethyl-2,3-dioxo-piperazine.

These processes suffer from the drawback of providing low yields of the desired product and, particularly, in the case of 1-chlorocarbonyl-4-ethyl-2,3-dioxo-piperazine, it is hard to prepare and handle, because of its sensitivity to moisture and the product is isolated with a relatively low purity, with complicated phosgene control, in view of the 1:1 stoichiometric ratio of the reaction.

It is an object of the invention to overcome the above mentioned limitations. This object is achieved with the preparation of the new urea, N,N'-carbonyl-bis-(4-ethyl-2,3-dioxo)-piperazine, of Formula I

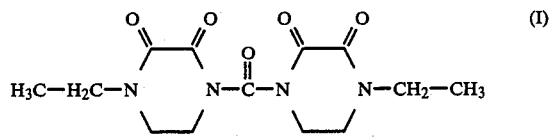

The symmetrical urea of Formula I is surprisingly reactive, allowing it to react with the amino group of an amino acid to give the corresponding amide, with a virtually quantitative yield.

Furthermore, N,N'-carbonyl-bis-(4-ethyl-2,3-dioxo)-piperazine is very stable, allowing it to be isolated, handled and stored.

The compound of Formula I, which is being disclosed for the first time in this invention, may be prepared by a process wherein a compound selected from the group formed by 4-ethyl-2,3-dioxo-piperazine and the trimethylsilyl derivative thereof is reacted with a compound selected from the group formed by carbonyl chloride and diphosgene.

This reaction is preferably conducted with at least two equivalents of the 4-ethyl-2,3-dioxo-piperazine trimethylsilyl derivative and one equivalent of carbonyl chloride or with at least two equivalents of the 4-ethyl-2,3-dioxo-piperazine trimethylsilyl derivative and one half equivalent of diphosgene.

Where it were considered desirable to exclude the use of phosgene, possible alternatives such as the reaction of disilylated bis-(2-ethylaminoethylene)urea with oxalyl chloride or dialkyl oxalate could be tried.

The fact that the urea of Formula I may be isolated allows the reactants of the synthesis to be correctly adjusted, which has a positive effect on the quality of the products obtained. The new, easy way of preparation of compounds of Formula II

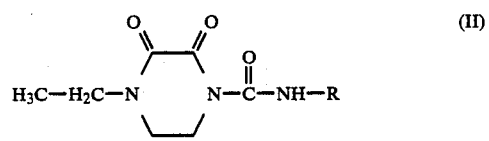

where R is as stated above, may be carried out by reacting the urea of Formula I with an amino acid selected from the group formed by an alpha-aminophenylacetic acid, an alpha-amino-p-hydroxyphenylacetic acid, a 6-(alpha-amino-phenylacetamido)-penicillanic acid and a 7-(alpha-amino-phenylacetamido)-cephalosporanic acid.

Among the said amino acids, there are deemed to be included 6-(alpha-amino-p-hydroxyphenylacetamido)-penicillanic, 7(alpha-amino-p-hydroxy-phenylacetamido)-cephalosporanic, 7-alpha-amino-(phenylacetamido)-7-betamethoxy-cephalosporanic acid, the trimethylsilyl derivatives thereof, their salts with tertiary or secondary amine organic bases or amidine.

Of particular interest are 7-amino-cephalosporanic and C-3 substituted 7-amino-7-methoxy cephalosporanic acids, preferably acetyloxymethyl, 5-(1-methyl-1,2,3,4-tetrazolyl)-thiomethyl methyl, carbamoyloxymethyl, 5-methyl-thiadiazol-2-mercaptomethyl, methoxy, chloro and azidomethyl.

The great interest in the use of the compound of Formula I for the preparation of compounds of formula II is to be found in the stability of the Formula I compound in comparison with the normally used reagents. This allows for an appropriate adjustment of reactants and operation, in the majority of cases, at room temperature.

Generally speaking, the Formula II compounds are penicillin and cephalosporin derivatives. When penicillins are used, the Formula I urea is reacted with an amino acid of formula III

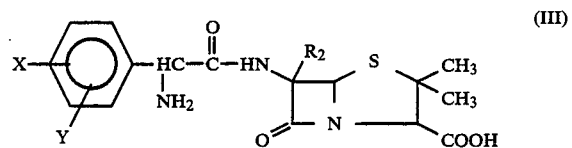

(III)

where X and Y may be the same or different and stand for hydrogen, hydroxyl or chlorine and $R_2$ stands for hydrogen, methoxy or formyl- amino.

When cephalosporins are used, the Formula I urea is reacted with an amino acid of formula IV

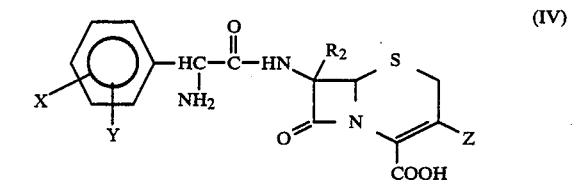

(IV)

where X, Y and $R_2$ are as stated above and Z is chlorine, methyl, acetyloxymethyl, methoxy, 5-(1-methyl-1,2,3,4-tetrazolyl)-thiomethyl, 2-(5-methyl-1,3,4-thiadiazolyl)-thiomethyl or —$CH_2R_4$, where $R_4$ is a group which may be introduced by nucleophilic substitution in the acetoxy of —$CH_2$—O—CO—$CH_3$.

The said penicillins and cephalosporins may be prepared also by reaction of the Formula I urea with a compound of Formula V

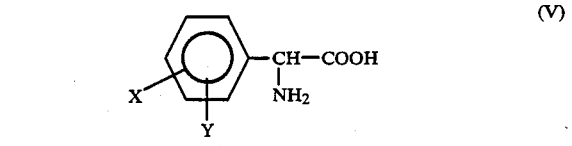

(V)

where X and Y are as stated above. The result of this reaction is the preparation of compounds of Formula VI

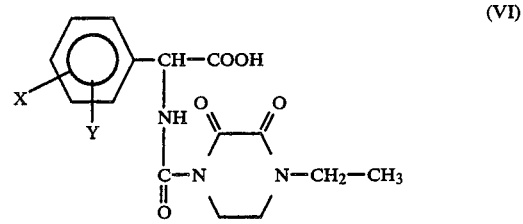

(VI)

where X and Y are as stated above.

The Formula VI compounds are converted into valuable intermediates since they may react with an acid chloride to give the corresponding mixed anhydride which is reacted with a 6-aminopenicillanic acid or a 7-aminocephalosporanic acid to give the corresponding penicillins or cephalosporins which may be isolated in acid form or converted into the corresponding sodium salts thereof.

Generally speaking, the Formula I urea is reacted with an amino acid where the carboxylic acid function is in the form of a salt of a tertiary amine, a secondary amine, cyclic or linear amidines or as the silyl ester.

Appropriate organic bases of tertiary and secondary amines are triethylamine and diethylamine. Appropriate amidines comprise the bicyclic amidines such as 1,8-diazabicyclo-(5,4,0)-undec-7-ene (DBU) and 1,5-diazabicyclo-(4,3,0) non-5-ene (DBN) or the linear amidines such as N,N,N',N'-tetramethylguanidine and N,N,N',N',N''-pentamethylguanidine. For the formation of trimethylsilyl derivatives, hexamethyldisilazane, trimethylbromosilane and trimethylchlorosilane are appropriate. The preferred solvent is dichloromethane.

There are given below a number of Examples of the invention without it being intended to limit the invention thereto.

EXAMPLE 1

N,N'-carbonyl-bis-(4-ethyl-2,3-dioxo)-piperazine 14.2 g of 4-ethyl-2,3-dioxo-piperazine, previously silylated with trimethylchlorosilane and triethylamine were added portionwise to a solution of 4.95 g of phosgene in 140 ml of dioxane.

The suspension was stirred for 24 hours at room temperature. The triethylamine hydrochloride was removed by filtration, leaving the title compound with a virtually quantitative yield. It was isolated from the solution containing it by concentration at reduced pressure.

The product exhibited the following characteristics:
Melting point: 199°–201° C.
IR (KBr) C=O ($cm^{-1}$): 1727 and 1670.
NMR ($H^1$) (in $CDCl_3$, values in ppm) delta: 1.18 (t, J=11 Hz, 3), 3.45 (dd, J=11 Hz, 2); area from 3.6 to 4.3 (4).
Elementary analysis: Calculated: C:50.32%, H:5.85%, N:18.06%. Found: C:50.30%, H:5.82%, N:18.19%.

EXAMPLE 2

N,N'-carbonyl-bis-(4-ethyl-2,3-dioxo)-piperazine 2.34 g of 4-ethyl-2,3-dioxo-piperazine were dissolved in 50 ml of dioxane and chilled to −20° C. Subsequently 2.13 ml of trimethylchlorosilane and 2.38 ml of triethylamine were added. The reaction mixture was stirred for 45 minutes at 0° C.

0.82 g of phosgene dissolved in dioxane was added. The suspension was stirred for 30 hours at room temperature. After removal of the triethylamine hydrochloride by filtration, a solution containing the title compound was obtained. The yield was virtually quantitative.

EXAMPLE 3

N,N'-carbonyl-bis-(4-ethyl-2,3-dioxo)-piperazine 2.34 g of 4-ethyl-2,3-dioxo-piperazine were dissolved in 50 ml of dichloromethane and chilled to −20° C. 2.13 ml of trimethylchlorosilane and 2.38 ml of triethylamine were added successively to the resulting solution. The reaction mixture was stirred for 45 minutes at 0° C. and chilled to −25°, −30° C.

3.38 g of 4-ethyl-2,3-dioxo-1-piperazine carbonyl chloride and 15 ml of dichloromethane were added and the mixture was stirred for 2 hours at 0° C. and 30 minutes at 20° C.

The solvent was removed from the reaction mixture by evaporation at reduced pressure and 50 ml of acetone were added to the residue. The mixture was stirred for 5 minutes at room temperature and filtered.

The solvent was removed from the resulting solution at reduced pressure and 50 ml of ethyl acetate were added to the residue. The mixture was stirred for 5 minutes at room temperature, filtered and washed with 15 ml of ethyl acetate and dried, to give 5.06 g of the title product (yield 99.0%), m.p. 199°–201° C.

EXAMPLE 4

N,N'-carbonyl-bis-(4-ethyl-2,3-dioxo)-piperazine 4.68 g of 4-ethyl-2,3-dioxo-piperazine were dissolved in 50 ml of dichloromethane and the resulting solution was chilled to −10° C. 8.40 ml of tributylamine and 4.40 ml of trimethylchlorosilane were added successively. The resulting solution was heated to 0°+5° C. and stirred for 45 minutes at that temperature.

0.1 ml of a 1% solution of 4-methyl-pyridine in dichloromethane was added to the reaction mixture, chilled to −25° C., and 5.14 g of a 30% solution of carbonyl chloride in monochloro-benzene was added dropwise over a period of 30 minutes.

When the addition was terminated, the reaction mixture was heated to 0°+5° C. and the reaction was completed by stirring for two hours at that temperature and 30 minutes at 20° C.

The solvent was removed from the resulting solution by evaporation at reduced pressure and 100 ml of ethyl acetate were added. The thus obtained suspension was stirred for two hours at 20°–25° C. and filtered. It was washed with 20 ml of ethyl acetate and dried, to give 4.74 g of the title product (Yield 98%).

EXAMPLE 5

N,N'-carbonyl-bis-(4-ethyl-2,3-dioxo)-piperazine 2.34 g of 4-ethyl-2,3-dioxo-piperazine were dissolved in 50 ml of dichloromethane and the resulting solution was chilled to −10° C. 4.19 ml of tributylamine and 2.20 ml of trimethylchlorosilane were added successively. The resulting solution was heated to 0°+5° C. and stirred for 45 minutes at that temperature.

The reaction mixture was chilled to −20° C. and 0.1 ml of a 1% solution of 4-methyl-pyridine in dichloromethane and 3.38 g of 4-ethyl-2,3-dioxo-1-piperazine carbonyl chloride. The mixture was heated to 0°–5° C. and the reaction was completed by stirring for two hours at that temperature and 30 minutes at 20° C.

The solvent was removed from the resulting solution by evaporation at reduced pressure and 100 ml of ethyl acetate were added. The thus obtained suspension was stirred for two hours at 20°–25° C. and filtered. It was washed with 20 ml of ethyl acetate and dried, to give 4.99 g of the title product. (Yield 97.6%)

EXAMPLE 6

N,N'-carbonyl-bis-(4-ethyl-2,3-dioxo)-piperazine 11.7 g of 4-ethyl-2,3-dioxo-piperazine were dissolved in 50 ml of dichloromethane and the resulting solution was chilled to −10° C. and 16.9 g of 4-ethyl-2,3-dioxo-1-piperazine carbonyl chloride and 5 ml of a 1% solution of 4-methyl-pyridine in dichloromethane were added thereto.

A solution of 19.6 ml of tributylamine in 50 ml of dichloromethane was added to the resulting solution dropwise over 15 minutes at −10°,−15° C.

The reaction was completed by stirring at −10°,−15° C. for a further 15 minutes.

The dichloromethane was removed from the resulting solution by evaporation at reduced pressure and 500 ml of ethyl acetate were added. The resulting suspension was stirred for two hours at 20°–25° C., was filtered and washed with 100 ml of ethyl acetate, to give 15.72 g of the title product (Yield 62%).

EXAMPLE 7

6-D(−)-alpha-(4-ethyl-2,3-dioxo-1-piperazinyl-carbonylamino-)phenylacetamido)-penicillanic acid (piperacillin)

0.92 g of anhydrous ampicillin was added at a temperature of 0°,+5° C. to a solution of 0.43 g of 1,8-diazabicyclo-(5,4,0)-undec-7-ene (DBU) in 10 ml of dichloromethane and the mixture was stirred for 1–2 minutes to obtain complete solution.

0.98 g of N,N'-carbonyl-bis-(4-ethyl-2,3-dioxo)-piperazine was added to the resulting solution, which was heated to 20°–25° C. and stirred for 5½ hours at that temperature.

HPLC analysis of the reaction mass revealed the total conversion of the starting ampicillin into the title product.

The dichloromethane was removed from the reaction mass by evaporation at reduced pressure and 23 ml of ethyl acetate, 12.5 ml of water and 6.5 ml of 1N HCl were added successively to the resulting residue, which was chilled to 0°,+5° C. The mixture was stirred for two hours at 0°,+5° C., was filtered, washed with 7.5 ml of 0.1N HCl and 25 ml of n-hexane and dried to give 1.24 g of the title product with $H_2O=3.45\%$ (alpha)=189.8°; isolation yield: 87.7%

EXAMPLE 8

6-(D(−)-alpha-(4-ethyl-2,3-dioxo-1-piperazinyl-carbonylamino)phenylacetamido)-penicillanic acid (piperacillin)

4.2 ml of hexamethyldisilazane were added to a suspension of 4.6 g of anhydrous ampicillin in 18 ml of methylene chloride. The mixture was refluxed for three hours, to give an almost complete solution. Subsequently there were added in one shot 4.90 g of N,N'- carbonyl-bis-(4-ethyl-2,3-dioxo)-piperazine and the mixture was stirred for six hours at 25°-30° C.

Liquid chromatography revealed the formation of the title compound with a virtually quantitative yield.

EXAMPLE 9

6-(D(—)-alpha-(4-ethyl-2,3-dioxo-1-piperazinyl-carbonylamino)-phenylacetamido)-penicillanic acid (piperacillin)

4.6 g of anhydrous ampicillin were suspended in 18 ml of methylene chloride, 1.8 ml of hexamethyldisilazane and 1.2 ml of trimethylchlorosilane were added. The mixture was heated under reflux for 3 hours. 4.9 g of N,N'-carbonyl-bis-(4-ethyl-2,3-dioxo)-piperazine were added to the thus obtained suspension, which was stirred for 6 hours at 20°-25° C.

Liquid chromatography revealed the formation of the title compound with a virtually quantitative yield.

EXAMPLE 10

D(—)-alpha-(4-ethyl-2,3-dioxo-1-piperazinyl-carbonylamino)-phenylacetic acid 0.93 ml of hexamethyldisilazane and 0.01 g of imidazole were added to a suspension of 0.60 g of D(—)-alfa-amino-phenylacetic acid in 15 ml of 1,2-dichloroethane.

The suspension was heated to reflux and stirred for 2½ hours. The resulting solution was cooled to 20°-25° C., 1.49 g of N,N'-carbonyl-bis-(4-ethyl-2,3-dioxo)-piperazine and 1 ml of 1,2-dichloroethane were added.

The reaction mixture was stirred for 5½ hours at 25° C. HPLC analysis of the reaction mass revealed a content of the title product that would correspond to a virtually quantitative yield.

10 ml of water and 4 ml of 1N HCl were added successively to the resulting system and it was cooled to 0°,+5° C. It was stirred for two hours at that temperature, filtered and washed with 5 ml of 0.1N HCl and 15 ml of n-hexane, to give 1.23 g of the title product, having a 5.63% water content; (alpha)= −26.12° (c=1% in 0.5N NaHCO$_3$). Isolation yield 91.6%

EXAMPLE 11

6-(D(—)-alpha-(4-ethyl-2,3-dioxo-1-piperazinyl-carbonylamino)-phenylacetamido)-penicillanic acid (piperacillin)

(A) 2.3 g of D(—)-alpha-(4-ethyl-2,3-dioxo-1-piperazinyl-carbonylamino)-phenylacetic acid (prepared according to Example 10) were suspended in 10 ml of dichloromethane and chilled to 0°. 0.8 ml of a 1% solution of 4-methyl-pyridine in dichloromethane and 0.97 ml of triethylamine were added successively and after stirring for 5 minutes gave a complete solution.

The reaction mixture was chilled to −25° C. and 0.89 ml of pivaloyl chloride were added.

The anhydride formation was completed by stirring for 20 minutes at −15°,−20° C. to give a white suspension. The system was chilled down to −35°,40° C.

(B) 1.72 g of 6-aminopenicillanic acid were suspended in 2.75 ml of dichloromethane and the resulting mixture was cooled to 3° C. 0.31 ml of water and 1.27 ml of triethylamine were added successively. Complete solution was obtained after stirring for 10 minutes at 10°-15°.

(C) The solution prepared according to (B) was added dropwise in 10 minutes over the anhydride prepared according to (A), holding the temperature to −35°,−40° C.

When the addition was terminated, the reaction mixture was stirred for 90 minutes at −30°,−35° C. and the dichloromethane was removed by evaporation at reduced pressure. 70 ml of ethyl acetate, 38 ml of water and 20 ml of 1N HCl were added successively to the resulting residue. The mixture was cooled to 0°,+5° C. and stirred for two hours at that temperature. The thus obtained suspension was filtered, washed with 25 ml of 0.1N HCl and 50 ml of n-hexane, to give 3.41 g of the title product with a water content (KF) of 5.45%; (alpha)=189.5° (anhydrous base). Isolation yield 86.4%.

EXAMPLE 12

6-(D(—)-alpha-(4-ethyl-2,3-dioxo-1-piperazinyl-carbonylamino)-phenylacetamido)-penicillanic acid (piperacillin)

1. Preparation of the mixed anhydride:

5.74 g of D(—)-alpha-(4-ethyl-2,3-dioxo-1-piperazinyl-carbonylamino)phenylacetic acid (prepared according to Example 10) were suspended in 30 ml of methylene chloride. The mixture was cooled to approximately 0° C. and 0.05 ml of pyridine and 2.45 ml of triethylamine were added. An almost colourless solution was obtained. It was chilled to −25° C. and 2.30 ml of pivaloyl chloride were added. The mass was stirred for 20 minutes at −10°/−15° C. This suspension was called preparation A.

2. 6-aminopenicillanic acid (6-APA) solution:

4.3 g of 6-APA were suspended in 10 ml of methylene chloride. The suspension was cooled down to approximately 0° C. and 2.7 ml of tetramethylguanidine were added. A solution formed almost immediately. This solution was called preparation B.

3. Acylation:

Preparation B was added dropwise over 15 minutes over preparation A after the latter had been chilled to −30°,−35° C. The mixture was stirred for two hours at −30°,−35° C. Chromatographic analysis revealed the formation of the title product with a virtually quantitative yield.

EXAMPLE 13

D(—)-alpha-4-ethyl-2,3-dioxo-1-piperazinyl-carbonylamino)-4-hydroxyphenylacetic acid 1.25 ml of hexamethyldisilazane and 0.01 g of imidazole were added to a suspension of 0.66 g of D(—)-alpha-amino-4-hydroxyphenylacetic acid in 15 ml of 1,2-dichloroethane and was heated to reflux. The reaction mixture was stirred under reflux for 3½ hours to give a complete solution. The solution was cooled to 20°-25° C. and 1.49 g of N,N'-carbonyl-bis-(4-ethyl-2,3-dioxo)-piperazine and 1 ml of 1,2-dichloroethane were added.

The reaction mixture was stirred for 5 hours at 25° C. HPLC analysis of the reaction mass revealed a title product content corresponding to a virtually quantitative yield.

10 ml of water and 5 ml of 1N HCl were added successively to the resulting system, with stirring for two hours at 0°,+5° C. it was filtered, washed with 0.1N HCl (5 ml) and thereafter with n-hexane (15 ml) to give 1.18 g of the title product with a water content of 0.28%; (alpha)= −38.9° (C=1% in 0.5N NaHCO$_3$). Isolation yield 89%

EXAMPLE 14

D(—)-alpha-(4-ethyl-2,3-dioxo-1-piperazinyl-carbonylamino)-4-hydroxyphenylacetic acid 2.2 g of p-hydroxyphenylglycine were suspended in 25 ml of methylene chloride, 0.1 g of imidazole and 4.2 ml of hexamethyldisilazane were added and the mixture was heated under reflux for a minimum of two hours. An almost complete solution was obtained, to which there was added 5.5 g of N,N'-carbonyl-bis-(4-ethyl-2,3-dioxo)-piperazine dissolved in 5 ml of methylene chloride, at 20°/25° C.

The mixture was stirred for 5 hours at 20°/25° C. Chromatographic analysis revealed the presence of the title compound, with a virtually quantitative yield.

EXAMPLE 15

7-(D-(—)-alpha-(4-ethyl-2,3-dioxo-1-piperazine-carboxamido)-alpha-(4-hydroxyphenyl)acetamido)-3-(((1-methyl-1H-tetrazol-5-yl)thio)methyl)-3-cephem-4-carboxylic acid (Cefoperazone)

(A) 3.02 g of D(—)-alpha-(4-ethyl-2,3-dioxo-1-piperazinyl-carbonylamino)-p-hydroxyphenylacetic acid (prepared as described in Examples 13 and 14) were suspended in 10 ml of dichloromethane and chilled to 0° C.

1.26 ml of triethylamine were added and the mixture was stirred for 15 minutes at 0°,+5° C. to give a white suspension.

1.0 ml of a 1% solution of 4-methyl-pyridine in dichloromethane was added and the system was chilled to −25°, −30° C.

1.13 ml of pivaloyl chloride were added and the anhydride formation reaction was completed by stirring for 30 minutes at −15° C.

The mixture was chilled to −50°, −55° C.

(B) 3.03 g of 7-alpha-amino-3-((1-methyl-1H-tetrazol-5-yl)-thio)-methyl-3-cephem-4-carboxylic acid were suspended in 12.5 ml of dichloromethane and 1.28 ml of N,N,N',N'-tetramethylguanidine were added. The reaction mixture was stirred at 20°-25° C. for 30 minutes to provide a complete solution.

(C) The solution prepared according to (B) was added dropwise over the mixed anhydride prepared according to (A) over a period of 25 minutes at −45°,−50° C. At the end of the addition, the reaction mixture was stirred for 30 minutes at −40°,−45° C. and for 50 hours at −20°,−22° C.

HPLC chromatographic analysis revealed the formation of the title compound with over 90% yield.

EXAMPLE 16

7-(D-(—)-alpha-(4-ethyl-2,3-dioxo-1-piperazine-carboxamido)-alpha-(4-hydroxyphenyl)acetamido)-3-(((1-methyl-1H-tetrazol-5-yl)thio)methyl)-3-cephem-4-carboxylic acid (Cefoperazone)

(A) 3.02 g of D(—)-alpha-(4-ethyl-2,3-dioxo-1-piperazinyl-carbonylamino)-p-hydroxyphenylacetic acid (prepared as described in Examples 13 and 14) were suspended in 10 ml of a mixture of dimethylacetamide and methylene chloride and chilled to 0° C.

1.26 ml of triethylamine were added and stirring was continued for 15 minutes at 0°,+5° C. to give a white suspension.

1.0 ml of a 1% solution of 4-methyl-pyridine in dichloromethane was added and the system was chilled to −25°,−30° C.

1.13 ml of pivaloyl chloride was added and the anhydride formation reaction was completed with stirring for 30 minutes at −15° C.

The mixture was chilled to −50°,−55° C.

(B) 3.03 g of 7-alpha-amino-3-(1-methyl-1H-tetrazol-5-yl)-thio)-methyl-3-cephem-4-carboxylic acid were suspended in 12.5 ml of dichloromethane and 1.28 ml of N,N,N',N'-tetramethylguanidine were added. The reaction mixture was stirred for 30 minutes at 20°-25° C. to provide a complete solution.

(C) The solution prepared according to (B) was added dropwise over the mixed anhydride prepared according to (A) over a period of 60 minutes at −40°/−50° C. Stirring was continued for 3 hours at −25°/−30° C. and for 10 hours at −10°/−15°. A solution containing the title compound with a yield of over 90% was obtained.

EXAMPLE 17

7-(D-(—)-alpha-(4-ethyl-2,3-dioxo-1-piperazine-carboxamido)-alpha-(4-hydroxyphenyl)acetamido)-3-(((1-methyl-1H-tetrazol-5-yl)thio)methyl)-3-cephem-4-carboxylic acid (Cefoperazone)

1.6 g of 1,8-diazabicyclo-(5,4,0)-undec-7-ene (DBU) were added to a suspension of 4.77 g of 7-(D(—)-alpha-amino-p-hydroxyphenylacetamido)-3-(((1-methyl-1H-tetrazol-5-yl)-methyl)-3-cephem-4-carboxylic acid in 15 ml of methylene chloride. The mixture was stirred for 30 minutes at 15°/25° C. Thereafter 3.5 g of N,N'-carbonyl-bis-(4-ethyl-2,3-dioxo)-piperazine were added with stirring at 20°/25° C. until the chromatographic analysis revealed the almost complete conversion of the starting cephalosporin into the title compound.

What we claim is:

1. N,N'-carbonyl-bis-(4-ethyl-2,3-dioxo)-piperazine of Formula I

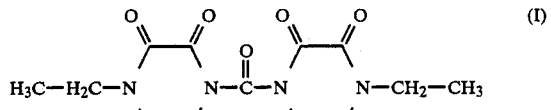

(I)

* * * * *